U S 0 1 1 4 2 6 3 7 8 B 2

US011426378B2

(12) United States Patent
Toledano et al.

(10) Patent No.: US 11,426,378 B2
(45) Date of Patent: Aug. 30, 2022

(54) METHOD FOR LONG-TERM TREATMENT OF ROSACEA

(71) Applicant: Sol-Gel Technologies Ltd., Ness Ziona (IL)

(72) Inventors: Ofer Toledano, Kfar Saba (IL); Ofra Levy-Hacham, Ness Ziona (IL); Ori Nov, Tarum (IL); Vered Ram, Rehovot (IL)

(73) Assignee: SOL-GEL TECHNOLOGIES LTD., Ness Ziona (IL)

( * ) Notice: Subject to any disclaimer, the term of this patent is extended or adjusted under 35 U.S.C. 154(b) by 181 days.

(21) Appl. No.: 16/794,887

(22) Filed: Feb. 19, 2020

(65) Prior Publication Data

US 2020/0261400 A1  Aug. 20, 2020

Related U.S. Application Data

(60) Provisional application No. 62/977,952, filed on Feb. 18, 2020, provisional application No. 62/977,974, (Continued)

(51) Int. Cl.
*A61K 31/327* (2006.01)
*A61P 17/10* (2006.01)
(Continued)

(52) U.S. Cl.
CPC .......... *A61K 31/327* (2013.01); *A61K 9/0014* (2013.01); *A61K 9/06* (2013.01);
(Continued)

(58) Field of Classification Search
None
See application file for complete search history.

(56) References Cited

U.S. PATENT DOCUMENTS 9,107,844 B2  8/2015  Clark et al.
9,439,857 B2  9/2016  Tamarkin et al.
(Continued)

FOREIGN PATENT DOCUMENTS

DE  202011100767 U1  12/2011
WO  2008/057411 A1  5/2008
(Continued)

OTHER PUBLICATIONS

International Search Report and Written Opinion dated Oct. 5, 2020 in International Patent Application No. PCT/IB2020/00119, 25 pages.
(Continued)

*Primary Examiner* — Nicole P Babson
(74) *Attorney, Agent, or Firm* — Sheppard, Mullin, Richter & Hampton LLP (57) ABSTRACT

A regimen for the long-term therapeutic treatment of rosacea. The regimen includes topically applying a pharmaceutical composition to the skin of a subject. The pharmaceutical composition includes about 1% w/w to about 10% w/w benzoyl peroxide as an active ingredient, and a pharmaceutically acceptable carrier or excipient. The benzoyl peroxide is the only active ingredient in the pharmaceutical composition, and the pharmaceutical composition is applied once daily for a period of about 52 weeks, to achieve, in a group of such subjects, a success rate of about 75%.

16 Claims, 2 Drawing Sheets

Related U.S. Application Data filed on Feb. 18, 2020, provisional application No. 62/972,896, filed on Feb. 11, 2020, provisional application No. 62/972,310, filed on Feb. 10, 2020, provisional application No. 62/960,384, filed on Jan. 13, 2020, provisional application No. 62/925,258, filed on Oct. 24, 2019, provisional application No. 62/871,286, filed on Jul. 8, 2019, provisional application No. 62/871,283, filed on Jul. 8, 2019, provisional application No. 62/807,356, filed on Feb. 19, 2019, provisional application No. 62/807,368, filed on Feb. 19, 2019.

(51) Int. Cl.
*A61K 9/107* (2006.01)
*A61K 9/00* (2006.01)
*A61K 9/06* (2006.01)
*A61P 17/00* (2006.01)
*A61K 9/50* (2006.01)
*A61K 9/10* (2006.01)

(52) U.S. Cl.
CPC .............. *A61K 9/10* (2013.01); *A61K 9/107* (2013.01); *A61K 9/50* (2013.01); *A61P 17/00* (2018.01); *A61P 17/10* (2018.01)

(56) References Cited

U.S. PATENT DOCUMENTS

| | | |
|---|---|---|
| 9,687,465 B2 | 6/2017 | Sertchook et al. |
| 9,693,988 B2 | 7/2017 | Chang et al. |
| 10,653,899 B2 | 5/2020 | Toledano et al. |
| 10,933,046 B2 | 3/2021 | Toledano et al. |
| 10,945,987 B2 | 3/2021 | Toledano et al. |
| 2004/0171561 A1 | 9/2004 | Popp |
| 2009/0306172 A1 | 12/2009 | Chang et al. |
| 2010/0016443 A1 | 1/2010 | Toledano et al. |
| 2010/0143285 A1 | 6/2010 | Mallard et al. |
| 2011/0052515 A1 | 3/2011 | Kaoukhov et al. |
| 2011/0262506 A1 | 10/2011 | Toledano et al. |
| 2012/0064135 A1 | 3/2012 | Levin et al. |
| 2013/0095185 A1 | 4/2013 | Toledano et al. |
| 2014/0121188 A1 | 5/2014 | Tamarkin et al. |
| 2014/0147396 A1 | 5/2014 | Sertchook et al. |
| 2017/0216282 A1 | 8/2017 | Dejovin et al. |
| 2017/0281571 A1 | 10/2017 | Sertchook et al. |
| 2018/0147165 A1 | 5/2018 | Sertchook et al. |
| 2020/0261397 A1 | 8/2020 | Toledano et al. |
| 2020/0383927 A1 | 12/2020 | Toledano et al. |
| 2020/0405665 A1 | 12/2020 | Sertchook et al. |
| 2021/0000741 A1 | 1/2021 | Shevachman et al. |
| 2021/0290985 A1 | 9/2021 | Toledano et al. |

FOREIGN PATENT DOCUMENTS

| | | |
|---|---|---|
| WO | 2008/093346 A2 | 8/2009 |
| WO | 2011/049547 A1 | 4/2011 |
| WO | 2011/101868 A2 | 8/2011 |
| WO | 2014/083557 A1 | 6/2014 |

OTHER PUBLICATIONS

International Search Report and Written Opinion dated May 19, 2020 in International Patent Application No. PCT/US2020/18906, 19 pages.

Matin, et al., "Benzoyl Peroxide"; Review from StatPearls Publishing, Treasure Island (FL), 4 pages (Feb. 6, 2019).

Wepierre, et al., "Distribution and dissociation of benzoyl peroxide in cutaneous tissue after application on skin in the hairless rat", International Journal of Cosmetic Science, vol. 8, pp. 97-104 (Jun. 1986).

Nacht, et al., "Benzoyl peroxide: Percutaneous penetration and metabolic disposition", Journal the American Academy of Dermatology, vol. 4, pp. 31-37 (Jan. 1981).

International Search Report and Written Opinion dated Jul. 15, 2020 in International Patent Application No. PCT/IB2020/00125, 16 pages.

International Search Report and Written Opinion dated Aug. 10, 2020 in International Patent Application No. PCT/IB2020/00118, 14 pages.

International Search Report and Written Opinion dated Aug. 12, 2020 in International Patent Application No. PCT/IB2020/00126, 19 pages.

International Search Report and Written Opinion dated Aug. 14, 2020 in International Patent Application No. PCT/IB2020/00123, 13 pages.

Montes, et al., "Topical Treatment of Acne Rosacea with Benzoyl Peroxide Acetone Gel," Therapeutics for the Clinician: New Reports on Treatment Modalities of Possible Interest to Patient-Caring Physicians, vol. 32, pp. 185-190 (1983).

Wilkin, et al., "Standard grading system for rosacea: Report of the National Rosacea Society Expert Committee on the Classification and Staging of Rosacea", Journal of the American Academy of Dermatology, vol. 50 (Jun. 2004), available at https://www.rosacea.org/physicians/grading-system-for-rosacea/view-online.

U.S. Non-Final Office Action dated May 28, 2020 in U.S. Appl. No. 16/794,809, 11 pages.

U.S. Non-Final Office Action dated Jul. 8, 2020 in U.S. Appl. No. 16/794,839, 9 pages.

Wollina, Uwe "Rosacea and rhinophyma in the elderly", Clinincs in Dermatology, vol. 29, pp. 61-68 (2011).

Oge, et al., "Rosacea: Diagnosis and Treatment," American Family Physician, vol. 92, pp. 187-198 (2015).

Gül, et al. "A case of granulomatous rosacea successfully treated with pimecrolimus cream", Journal of Dermatological Treatment, vol. 19, pp. 313-315 (2008).

Wester, et al., "Controlled release of benzoyl peroxide from a porous microsphere polymeric system can reduce topical irritancy", Journal of the American Academy of Dermatology, vol. 24, pp. 720-726 (1991).

Sawleshwarkar, et al., "Multicenter study to evaluate efficacy and irritation potential of benzoyl peroxide 4% cream in hydrophase base (Brevoxyl) in acne vulgaris," Indian Journal of Dermatology, Venereology and Leprology, vol. 69, pp. 19-22 (2003).

Breneman, et al., "Double-blind, randomized, vehicle-controlled clinical trial of once-daily benzoyl peroxide/clindamycin topical gel in the treatment of patients with moderate to severe rosacea," International Journal of Dermatology, vol. 43, pp. 381-387 (2004).

Gold, et al., P161 "Use of Benzoyl Peroxide/Clindamycin gel in the once daily treatment of moderate rosacea," Journal of the American Academy of Dermatology, vol. 52, suppl. P25 (2005).

Leyden, et al., P53 "Blinded photographic review for a double blind, multicenter, placebo-controlled study comparing Benzoyl Peroxide/Clindamycin and placebo for the treatment of rosacea," Journal of the American Academy of Dermatology, vol. 52, suppl. P14 (2004).

Goldgar, et al., "Treatment Options for Acne Rosacea," American Family Physician, vol. 80, pp. 461-468 (2009).

Crawford, et al., "Rosacea: I. Etiology, pathogenesis, and subtype classification," Journal of the American Academy of Dermatology, vol. 51, pp. 327-341 (2004).

McGregor, et al., "A Review of the Current Modalities of the Treatment of Papulopustular Rosacea," Dermatologic Clinics, vol. 36, 16 pages (2017).

Feaster, et al., "Clinical effectiveness of novel rosacea therapies," Current Opinion in Pharmacology, vol. 46, pp. 14-18 (2019).

Del Rosso, et al., "Update on the Management of Rosacea from the American Acne & Rosacea Society (AARS)", The Journal of Clinical & Aesthetic Dermatology, vol. 12, pp. 17-24 (2019).

James, et al., "Rosacea", Andrews' Diseases of the Skin: Clinical Dermatology, 10th ed., Saunders Elsevier, pp. 239-248 (2005).

International Search Report and Written Opinion dated Aug. 28, 2020 in International Patent Application No. PCT/IB2020/00120, 15 pages.

(56) References Cited

OTHER PUBLICATIONS

U.S. Non-Final Office Action dated Jul. 7, 2020 in U.S. Appl. No. 16/794,734, 8 pages.
Nicholson, K. et al., "A pilot quality-of-life instrument for acne rosacea", Journal of the American Academy of Dermatology, vol. 47, No.2, 213-221.(2007).
Non-Final Office Action dated Apr. 11, 2022 in U.S. Appl. No. 16/794,923, 28 pages.

METHOD FOR LONG-TERM TREATMENT OF ROSACEA

CROSS-REFERENCE TO RELATED APPLICATIONS

This application claims priority under 35 U.S.C. § 119(e) from U.S. Provisional Application No. 62/977,974, filed Feb. 18, 2020, U.S. Provisional Application No. 62/977,952, filed Feb. 18, 2020, U.S. Provisional Application No. 62/972,896, filed Feb. 11, 2020, U.S. Provisional Application No. 62/972,310, filed Feb. 10, 2020, U.S. Provisional Application No. 62/960,384, filed Jan. 13, 2020, U.S. Provisional Application No. 62/925,258, filed Oct. 24, 2019, U.S. Provisional 62/871,286, filed Jul. 8, 2019, U.S. Provisional 62/871,283, filed Jul. 8, 2019, U.S. Provisional 62/807,356, filed Feb. 19, 2019, and U.S. Provisional 62/807,368, filed Feb. 19, 2019, the contents of which are incorporated in their entirety as if fully set forth herein.

TECHNICAL FIELD

This application relates to methods for the long-term therapeutic treatment of skin conditions and afflictions, such as rosacea, including moderate to severe rosacea, and symptoms and considerations associated therewith, including topically applying to the skin of a subject in need of said treatment a pharmaceutical composition comprising benzoyl peroxide.

BACKGROUND

Rosacea is a chronic disease of inflammatory dermatitis that mainly affects the median part of the face and the eyelids of certain adults. It is characterized by telangiectatic erythema, dryness of the skin, papules and pustules. Conventionally, rosacea develops in adults from the ages of 30 to 50, and more frequently affects women, although the condition is generally more severe in men. Rosacea is a primitively vascular condition whose inflammatory stage lacks the cysts and comedones characteristic of common acne.

Factors that have been described as possibly contributing towards the development of rosacea include, for example: the presence of parasites such as the *Demodex folliculorum*; the presence of bacteria such as *Helicobacter pylori* (a bacterium associated with gastrointestinal disorders); hormonal factors (such as endocrine factors); climatic and immunological factors; and so forth.

Rosacea develops in four stages over several years, in spasms aggravated by variations in temperature, alcohol, spices, exposure to sunlight and stress. The various stages of the disease are:

Stage 1 (stage of erythema episodes): the patients have erythrosis spasms due to the sudden dilation of the arterioles of the face, which then take on a congestive, red appearance. These spasms are caused by emotions, meals and temperature changes.

Stage 2 (stage of couperosis, i.e., of permanent erythema with telangiectasia): certain patients also have oedema on the cheeks and the forehead.

Stage 3 (inflammatory stage, papulopustular rosacea): patients exhibit appearance of inflammatory papules and pustules, but without affecting the sebaceous follicles, and thus, does not include cysts and comedones.

Stage 4 (rhinophyma stage): this late phase essentially affects men. The patients have a bumpy, voluminous red nose with sebaceous hyperplasia and fibrous reordering of the connective tissue.

Typical treatment of rosacea includes oral or topical administration of antibiotics such as tetracyclines, salicylic acid, anti-fungal agents, steroids, metronidazole (an antibacterial agent) and isotretinoin, or treatment with anti-infectious agents such as azelaic acid.

SUMMARY

An exemplary embodiment of this application is directed to regimen for the long-term therapeutic treatment of rosacea, the regimen comprising topically applying to the skin of a subject in need of said treatment a pharmaceutical composition, the pharmaceutical composition comprising about 1% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is applied once daily for a period of up to about 52 weeks, about 40 weeks to about 52 weeks, about 44 weeks to about 52 weeks, about 48 weeks to about 52 weeks, or about 40 weeks, about 44 weeks, about 48 weeks, about 52 weeks, in a group of such subjects, a success rate of about 50% to about 85%, about 50% to about 75%, about 60 to about 75%, about 70% to about 75%, or about 50%, about 55%, about 60%, about 65%, about 70%, about 75%, wherein the success rate is defined as a percentage of the number of subjects achieving clear or almost clear skin on the investor global assessment (IGA) scale after treatment with the pharmaceutical composition.

In other exemplary embodiments, the benzoyl peroxide is the sole active ingredient administered to the subject during the duration of the regimen.

In other exemplary embodiments, the pharmaceutical composition comprises about 2.5% w/w to about 10% w/w of benzoyl peroxide, preferably about 2.5% w/w to about 10% w/w of benzoyl peroxide, and more preferably about 5% w/w of benzoyl peroxide.

In other exemplary embodiments, the benzoyl peroxide is selected from solid, solution or suspension form.

In other exemplary embodiments, the regimen can be used as a first line therapy for the treatment of rosacea.

In other exemplary embodiments, the severe rosacea can be any one of erythematotelengietatic rosacea, papulopustular rosacea, phymatous rosacea or ocular rosacea.

In other exemplary embodiments, the pharmaceutical composition can be a cream or an emulsion.

In other exemplary embodiments, the pharmaceutical composition is an extended release formulation. The extended-release can be obtained by encapsulation, microencapsulation, microspheres, coating, combinations thereof and the like. The benzoyl peroxide can be encapsulated or microencapsulated, the benzoyl peroxide can be included in a microsphere, a coating, a combination thereof and the like.

In other exemplary embodiments, the rosacea is moderate to severe rosacea.

In another exemplary embodiment, the percentage of subjects having no adverse effects after treatment with the pharmaceutical composition for up to about 52 weeks, including for about 40 weeks, about 44 weeks, or about 48 weeks, is at least 75%, preferably between about 75% to about 90%, between about 75% to about 85%, between about 80% to about 85%.

In another exemplary embodiment, the adverse effect is selected from stinging and/or burning, dryness and itching.

Details of other exemplary embodiments of the present disclosure will be included in the following detailed description and the accompanying figures. It is appreciated that certain features of the exemplary embodiments described in this application, which are, for clarity, described in the context of separate embodiments, can also be provided in combination in a single embodiment.

BRIEF DESCRIPTION OF THE DRAWINGS

In order to understand the disclosure and to see how it can be carried out in practice, embodiments will now be described, by way of non-limiting examples only, with reference to the accompanying drawings, in which.

DETAILED DESCRIPTION

Multiple studies have been directed to the treatment of rosacea using a pharmaceutical or dermatological active agent such as metronidazole, azelaic acid, sulfacetamide, brimonidine, ivermectin, permethrin and clindamycin, and with doxycycline, which is identified as the only FDA-approved treatment for rosacea (Oge et al., "Rosacea: Diagnosis and Treatment," *American Family Physician*, v. 92(3), pp. 187-198 (2015); Gul et al., "A case of granulomatous rosacea successfully treated with pimecrolimus cream," *J. Derm. Treatment*, 19, 313-315 (2008)).

Benzoyl peroxide (BPO) is generally identified as an anti-acne agent, used alone (U.S. Pat. No. 9,439,857; Wester et al., "Controlled release of benzoyl peroxide from a porous microsphere polymeric system can reduce topical irritancy," *J. Am. Acad. Derma.* 24, 720-726 (1991); Sawleshwarkar, "Multicenter study to evaluate efficacy and irritation potential of benzoyl peroxide 4% cream in hydrophase base (Brevoxyl) in acne vulgaris," *Ind. J. Derm. Vener. Lepro.*, 69(1), 19-22 (2003)) or in combination with a primary active such as avermectin (U.S. 2011/0052515).

One such study includes a therapeutic regimen involving treatment of acne rosacea in a group of patients in need of such treatment with 5% BPO-acetone gel for four weeks, followed by treatment of the same group of patients with 10% BPO-acetone gel for an additional four weeks. (Montes et al., "Topical Treatment of Acne Rosacea with Benzoyl Peroxide Acetone Gel," *Therapeutics for the Clinician: New Reports on Treatment Modalities of Possible Interest to Patient-Caring Physicians*, 32, 185-190 (1983)). The Montes study showed a significantly better response during the five to eight weeks of treatment with 10% BPO-acetone gel compared to the first four weeks of treatment with 5% BPO-acetone gel. Moreover, although Montes 1983 claims success in the treatment of rosacea using a BPO-acetone gel, 25% of the patients in the study showed no improvement and 40% of the patients developed an irritation. Additionally, this study required increasing the amount of BPO administered to the patients from 5% to 10% after week four. The results of the Montes 1983 study make it clear that BPO would not be suitable for regular use in the treatment of rosacea, especially as a first line treatment of rosacea.

Other studies show that, when used in the treatment of rosacea, BPO is generally combined with a primary active agent such as clindamycin (Breneman et al., "Double-blind, randomized, vehicle-controlled clinical trial of once-daily benzoyl peroxide/clindamycin topical gel in the treatment of patients with severe rosacea," *Int. J. Derm.*, 43, 381-387 (2004); Gold et al., "Use of Benzoyl Peroxide/Clindamycin gel in the once daily treatment of moderate rosacea," *J. Amer. Acad. Dermat.*, 52(3), sup., P25 (2004); Leyden et al., "Blind photographic review for a double blind, multicenter, placebo-controlled study comparing Benzoyl Peroxide/Clindamycin and placebo for the treatment of rosacea," *J. Amer. Acad. Dermat.*, 52(3), sup., P14 (2004); Goldgar et al., "Treatment Options for Acne Rosacea," *J. Amer. Fam. Physician*, 80(5), 461-468 (2009)).

BPO is generally identified as only a possible second-line treatment of rosacea following the use of another, different active. (Oge 2015, Table 5; Goldgar 2009, "Key Recommendations for Practice"). When BPO was used as the sole active agent for the treatment of rosacea, lesions were found to be unresponsive. (Gul 2008).

These previous rosacea treatments with BPO alone or in combination with other agents, have been shown to have several drawbacks such as irritation and intolerance phenomena, especially when they are administered for a prolonged period. (Crawford et al., "Rosacea: I. Etiology, pathogenesis, and subtype classification," *J. Am. Acad. Dermatol.*, 51, 327-341 (2004)). These treatments are only suppressive and not curative, acting especially on the pustulous spasms occurring during the inflammatory stage.

Such drawbacks associated with the treatment of rosacea involving the use of BPO result in exclusion of BPO from standard rosacea treatment methods. For example, "A Review of the Current Modalities for the Treatment of Papulopustular Rosacea" identifies metronidazole, ivermectin and azelaic acid as topical therapies that were proven effective for the treatment of rosacea. (McGregor et al., "A Review of the Current Modalities of the Treatment of Papulopustular Rosacea," *Dermatol. Clin.* (2017)). While McGregor 2017 mentions alternate therapies, such as sodium sulfacetanide/sulfur cream, clindamycin, tretinoin, calcineurin inhibitors and oral tretinoin, that may have some effectiveness in the treatment of rosacea, notably, McGregor 2017 does not include, or even mention, BPO in the long list of possible treatment therapies described therein. The absence of BPO as a known treatment for rosacea is also evident in other studies. (Feaster et al., "Clinical effectiveness of novel rosacea therapies," *Current Op. Pharmacol.*, 46, 14-18 (2019); Del Rosso et al., "Update on the Management of Rosacea from the American Acne & Rosacea Society (AARS); *J. Clinical & Aesthetic Dermat.*, 12 (6), 17-24 (2019)). The absence of BPO as a recognized first-line treatment for rosacea is especially evident in Del Rosso, which is a well-known and respected authority on the treatment of rosacea. The AARS review lists the Society's recommendation for rosacea treatment, including topical metronidazole, topical azelaic acid, oral tetracyclines, ivermectin, topical alpha agonists, and oral isotretinoin, as well as "alternative therapies," such as sulfacetamide/sulfur, calcineurin inhibitors, retinoids, and permethrin. (See e.g., Table 1 of the AARS review.) BPO is not mentioned in the AARS review either as a leading, or even an alternative, therapeutic agent for the treatment of rosacea.

Considering the chronic nature of rosacea, there is a need for long-term treatment of the disease, its symptoms and associated conditions, in a safe and effective manner. Thus, there exists a need for compositions that have long-term, and improved, efficacy in the treatment of rosacea, that impart greater tolerance to the active principles and that reduce, substantially minimize or do not have the side effects described in the prior art. There also exists a need for long-term, prolonged treatment of rosacea without any accompany adverse effects.

Advantages and features of the present disclosure, and methods for accomplishing the same will be more clearly understood from exemplary embodiments described below with reference to any accompanying figures. However, the present disclosure is not limited to the following exemplary embodiments and can be implemented in various different forms. The exemplary embodiments are provided only to provide sufficient disclosure of the present discoveries and to fully provide a person having ordinary skill in the art to which the present disclosure pertains within the technical field, and the present disclosure will be defined by any appended claims and combinations thereof.

As used herein, like reference numerals generally denote like elements throughout the present specification. Further, in the following description, a detailed explanation of well-known related technologies can be omitted to avoid unnecessarily obscuring the subject matter of the present disclosure.

As used herein, terms such as "including" and "having" are generally intended to allow other components to be included unless the terms are used in conjunction with the term "only."

As used herein, the term "topical use" is meant to encompass the topical administration of an exemplary composition by formulating said composition in any way known in the art, or in formulations disclosed herein, which are compatible with the skin, mucous membranes and/or the integuments.

As used herein, the term "treating" or "treatment" includes curing a condition, treating a condition, preventing or substantially preventing a condition, treating symptoms of a condition, curing symptoms of a condition, ameliorating, reducing and/or minimizing symptoms of a condition, treating effects of a condition, ameliorating, reducing and/or minimizing effects of a condition, and preventing and/or substantially preventing results of a condition, As used herein, the term "first-line therapy" or "first-line treatment" means a therapy or treatment for which its label does not include a requirement or recommendation that said therapy or treatment should be used only after other therapies or treatments were shown to be unsatisfactory or unsuccessful. It can also include a therapy and/or treatment wherein no other actives (beyond the main active) are administered to the individual subject in need.

As used herein, the term "success rate" corresponds to of the sum of the number of subjects achieving clear and the number of subject achieving almost clear skin on the investor global assessment (IGA) scale after treatment with the pharmaceutical composition, which can also be represented as a percentage of study subjects.

As used herein, the term "early onset" or "early onset of action" means achieving a desired result and/or effect at a point in time that is earlier or even much early than achieved using a vehicle or other, conventional treatment approach. For example, it can mean achieving a desired result and/or effect no later than about 8 weeks from initial treatment, preferably no later than about 4 weeks from initial treatment, and more preferably no later than about 2 weeks from initial treatment.

As used herein, the term "pharmaceutical composition" refers to a composition comprising one or more active ingredients with other components such as, for example, pharmaceutically acceptable ingredients and/or excipients.

The purpose of a pharmaceutical composition is to facilitate administration of an active ingredient to a subject.

As used herein, the terms "pharmaceutically active agent" or "active agent" or "active pharmaceutical ingredient" are interchangeable and mean the ingredient is a pharmaceutical drug, which is biologically- and/or chemically-active and is regulatory-approved or approvable as such.

As used herein, the term "ingredient" refers to a pharmaceutically acceptable ingredient, which is included or is amenable to be included in The FDA's Inactive Ingredient (IIG) database. Inactive ingredients can sometimes exhibit some therapeutic effects, although they are not drugs.

As used herein, the term "adverse events values" refers to an average percentage of subjects that experience any adverse events associated with the treatment of rosacea with a composition described and/or claimed herein (usually on a surface of the skin of a subject treated with a composition described and/or claimed herein). A non-limiting list of such adverse events includes: irritation, dryness, scaling, itching purities, burning, stinging, combinations thereof and the like.

As used herein, the term "long-term" indicates prolonged use of a pharmaceutical ingredient for at least about 12 weeks or longer, at least about 40 weeks or longer, and more preferably at least about 52 weeks or longer, in a treatment regimen.

As used herein, the term "inflammatory lesion" refers to papules and pustules present on the skin of a patient, and does not include nodules and cysts.

As used herein, the term "papule" refers to a solid, elevated inflammatory lesion equal to or less than about 5 mm in diameter.

As used herein, the term "pustule" refers to an elevated inflammatory, pus-containing lesion equal to or less than about 5 mm in diameter.

As used herein, the term "nodule" and/or "cyst" refers to palpable solid inflammatory lesion, greater than about 5 mm in diameter. The nodule and/or cyst may have depth but does not necessarily include elevation.

Whenever a numerical range is indicated herewith, it is meant to include any cited numeral (fractional or integral) within the indicated range. The phrases "ranging/ranges between" a first indicated number and a second indicated number and "ranging/ranges from" a first indicated number "to" a second indicated number are used herein interchangeable and are meant to include the first and second indicated numbers and all fractional and integral numerals therebetween.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "10 μm" is intended to mean "about 10 μm."

As used herein, numbers and/or numerical ranges preceded by the term "about" should not be considered to be limited to the recited range. Rather, numbers and/or numerical ranges preceded by the term "about" should be understood to include a range accepted by those skilled in the art for any given element in formations according to the subject invention.

As used herein, when a numerical value is preceded by the term "about," the term "about" is intended to indicate +/−10%.

As used herein, the singular form "a," "an" and "the" include plural references unless the context clearly dictates otherwise. For example, the term "a compound" or "at least one compound" can include a plurality of compounds, including combinations and/or mixtures thereof.

As used herein, the term "method" refers to manners, means, techniques and procedures for accomplishing a given task including, but not limited to, those manners, means, technical and procedures either known to, or readily developed from known manners, means, techniques and procedures by practitioners of the chemical, pharmacological, biological, biochemical and medical arts.

It is appreciated that certain features of the exemplary embodiments described herein, which are, for clarity, described in the context of separate embodiments, can also be provided in combination in a single embodiment. Conversely, various features of the exemplary embodiments, which are, for brevity, described in the context of a single embodiment, can also be provided separately or in any suitable sub-combination or as suitable in any other described embodiment. Certain features described in the context of various embodiments are not to be considered essential features of those embodiments, unless the embodiment is inoperative without those elements.

An exemplary embodiment of this application is directed to regimen for the long-term therapeutic treatment of rosacea, the regimen comprising topically applying to the skin of a subject in need of said treatment a pharmaceutical composition, the pharmaceutical composition comprising about 1% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is applied once daily for a period of up to about 52 weeks, about 40 weeks to about 52 weeks, about 44 weeks to about 52 weeks, about 48 weeks to about 52 weeks, or about 40 weeks, about 44 weeks, about 48 weeks, about 52 weeks, in a group of such subjects, a success rate of about 50% to about 85%, about 50% to about 75%, about 60 to about 75%, about 70% to about 75%, or about 50%, about 55%, about 60%, about 65%, about 70%, about 75%, wherein the success rate is defined as a percentage of the number of subjects achieving clear or almost clear skin on the investor global assessment (IGA) scale after treatment with the pharmaceutical composition.

In other exemplary embodiments, the benzoyl peroxide is the sole active ingredient administered to the subject during the duration of the regimen.

In other exemplary embodiments, the pharmaceutical composition comprises about 2.5% w/w to about 10% w/w of benzoyl peroxide, preferably about 2.5% w/w to about 10% w/w of benzoyl peroxide, and more preferably about 5% w/w of benzoyl peroxide.

In other exemplary embodiments, the benzoyl peroxide is selected from solid, solution or suspension form.

In other exemplary embodiments, the regimen can be used as a first line therapy for the treatment of rosacea.

In other exemplary embodiments, the rosacea can be any one of erythematotelengietatic rosacea, papulopustular rosacea, phymatous rosaca or ocular rosacea.

In other exemplary embodiments, the pharmaceutical composition can be a cream or an emulsion.

In other exemplary embodiments, the pharmaceutical composition is an extended release formulation. The extended-release can be obtained by encapsulation, microencapsulation, microspheres, coating, combinations thereof and the like. The benzoyl peroxide can be encapsulated or microencapsulated, the benzoyl peroxide can be included in a microsphere, a coating, a combination thereof and the like.

In other exemplary embodiments, the rosacea is moderate to severe rosacea.

In another exemplary embodiment, the percentage of subjects having no adverse effects after treatment with the pharmaceutical composition for up to about 52 weeks, including for about 40 weeks, about 44 weeks, or about 48 weeks, is at least 75%, preferably between about 75% to about 90%, between about 75% to about 85%, between about 80% to about 85%.

In another exemplary embodiment, the adverse effect is selected from stinging and/or burning, dryness and itching.

In some further embodiments, the composition further comprises at least one non pharmaceutical active additive selected from the group consisting of chelating agents, antioxidants, sunscreens, preservatives, fillers, electrolytes, humectants, dyes, mineral or organic acids or bases, fragrances, essential oils, moisturizers, vitamins, essential fatty acids, sphingolipids, self-tanning compounds, calmatives and skin-protecting agents, pro-penetrating agents and gelling agents, or a mixture and/or combination thereof.

In other embodiments, the composition is formulated into a topically applicable, physiologically acceptable medium comprising of: (a) at least one member selected from the group consisting of water, alcohols, oils, fatty substances and waxes; and (b) at least one additive selected from the group consisting of chelating agents, antioxidants, sunscreens, preservatives, fillers, electrolytes, humectants, dyes, mineral acids, mineral bases, organic acids, organic bases, fragrances, essential oils, moisturizers, vitamins, essential fatty acids, sphingolipids, self-tanning compounds, calmatives, skin-protecting agents, pro-penetrating agents, gelling agents, emulsifiers, co-emulsifiers, and mixtures and/or combinations thereof.

In some embodiments the composition is formulated as an emulsion (including an oil-in-water emulsion, a water-in-oil emulsion, multiple emulsions and microemulsions). In other embodiments, the composition is formulated as a cream.

The compositions described in exemplary embodiments herein are pharmaceutical compositions, and especially dermatological compositions, which can be in any galenical form conventionally used for topical application. By addition of a fatty or oily phase, they can also be in the form of dispersions of the lotion or serum type, emulsions of liquid or semi-liquid consistency of the milk type obtained by dispersing a fatty phase in an aqueous phase (O/W) or conversely (W/O), or suspensions or emulsions of soft, semiliquid or solid consistency of the cream, gel or ointment type, or alternatively multiple emulsions (W/O/W or O/W/O), microemulsions, microcapsules, microparticles and/or vesicular dispersions of ionic and/or nonionic type, and/or wax/aqueous phase dispersions. These compositions are formulated according to the usual methods.

In further embodiments, the composition comprises, as a single pharmaceutical active agent, benzoyl peroxide in a solid form, for topical use in the treatment of rosacea, is an oil in water emulsion comprising a polyoxylstearate and a glycerylstearate. Various methods for the preparation of the BPO-containing compositions are described in U.S. Application Publication Nos. 2010/0016443, 2017/0281571 and 2018/0147165 and U.S. Pat. No. 9,687,465.

In some embodiments, the ratio of said polyoxylstearate to said glycerylstearate is in the range of about 0.1:10 to about 10:0.1.

In yet further embodiments, said polyoxylstearate is selected from the group consisting of Polyoxyl-8 stearate, Polyoxyl-20 stearate, Polyoxyl-40 stearate, Polyoxyl-100 stearate and combinations and/or mixtures thereof.

In further embodiments, said glycerylstearate is selected from the group consisting of glyceryl mono-stearate, glyceryl di-stearate and combinations and/or mixtures thereof.

In other embodiments, said polyoxylstearate in said composition is in the range of from about 0.1% w/w to about 30% w/w.

In further embodiments, the amount of said glycerylstearate in said composition is in the range of from about 0.1% w/w to about 30% w/w.

In other embodiments, said composition further comprises at least one fatty alcohol.

In other embodiments, said at least one fatty alcohol is selected from the group consisting of octyl alcohol, 2-ethyl hexanol. nonyl alcohol, decyl alcohol, undecanol, dodecyl alcohol, tridecyl alcohol, tetradecyl alcohol, pentadecyl alcohol, cetyl alcohol, palmitoleyl alcohol, heptadecyl alcohol, cetostearyl alcohol, stearyl alcohol, isostearyl alcohol, elaidyl alcohol, oleyl alcohol, linoleyl alcohol, elaidolinolenyl alcohol, ricinoleyl alcohol, nonadecyl alcohol, arachidyl alcohol, heneicosyl alcohol. behenyl alcohol, erucyl alcohol, lignoceryl alcohol, ceryl alcohol, montanyl alcohol, cluytyl alcohol, myricyl alcohol, melissyl alcohol, geddyl alcohol, cetearyl alcohol and combinations and/or mixtures thereof.

In further embodiments, the amount of said at least one fatty alcohol in said composition is in the range of from about 0.2% w/w to about 50% w/w.

In yet other embodiments, said composition further comprises a polyacrylic acid homopolymer or copolymer.

In other embodiments, said oil in said oil in water emulsion is selected from the group consisting of paraffin oil, isopropyl myristate, caprylic/capric triglyceride, squalane, squalene, almond oil, castor oil, olive oil, jojoba oil, sunflower oil, soybean oil, grape seed oil, dimethicone, cyclomethicone and combinations and/or mixtures thereof.

In further embodiments, said oil in present in the composition in an amount in the range of from about 0.05% w/w to about 50% w/w.

In some embodiments, said water in said oil in water emulsion further comprises at least one water soluble humectant.

In other embodiments, said at least one water soluble humectant is selected from the group consisting of propylene glycol, glycerin, polyethylene glycol-X and combinations and/or mixtures thereof, where X is in the range of from about 200 to about 10,000.

In some embodiments, the composition comprises said solid BPO in a controlled and/or slowed release drug delivery system. In further embodiments, said controlled and/or slowed release drug delivery system is an encapsulation in a microcapsule, wherein said solid BPO is embedded in said microcapsule. When referring to a "controlled and/or slowed release drug delivery system" it should be understood to relate to a delivery system (which in the present application is a topical delivery system) that enables the release of the pharmaceutical active agent in predetermined amounts over a specified period. In some embodiments, said system is a core-shell system of a microcapsule and/or a porous matrix structure, such as, for example, a microsponge. The term "embedded" should be understood to encompass an inert system that provides a barrier between the pharmaceutical active agent, i.e. BPO, and its surrounding environment in the composition. In some embodiments, said agent is entrapped and/or encapsulated in said controlled release system.

In some embodiments, said core of said microcapsule comprises or consists of said solid BPO.

In some further embodiments, said microcapsules are a core shell microcapsule. The shell comprises at least one inorganic polymer. In some other embodiments, said inorganic polymer of said shell is a metal oxide or semi-metal oxide shell (layer).

In some embodiments, said microcapsule comprises a metal oxide or semi-metal oxide coating or layer (shell) and a core comprising or consisting of solid BPO.

In some embodiments, said microcapsule comprises a metal oxide or semi-metal oxide coating or layer (shell) and a core comprising solid BPO is prepared by a process comprising the steps of:

(a) contacting a solid BPO particulate matter with an ionic additive and an aqueous medium to obtain a dispersion of said particulate matter having positive charges on its surface;

(b) subjecting the particulate matter to a coating procedure comprising precipitating a metal oxide salt onto the surface of the particulate matter to form a metal oxide layer thereon thereby to obtain particulate matter coated by a metal oxide coating layer;

(c) repeating step (b) at least 4 more times: and (d) aging said coating layer.

As used herein, the term "solid BPO particulate matter" refers to a solid BPO having solubility in water of less than about 1% w/w, typically less than about 0.5% and at times less than about 0.1% w/w at room temperature (about 20° C.). The "solid BPO particulate matter" constitutes the "core" of the particles obtained by the process. The solid BPO particulate matter, is, in some embodiments, in such a state of subdivision that it can be suspended in water, e.g., in the form of a finely-divided powder having a $D_{90}$ (see definition below), in some embodiments in the range of from about 0.3 to about 50 microns. Such a particulate matter can be readily suspended in an aqueous systems by stirring, with or without the aid of a surfactant.

The terms "solid BPO particulate matter" and "particulate matter" will be used interchangeably.

In the present application, the terms "layer", "coating" or "shell" and similar terms, refer to a layer of metal oxide or semi-metal oxide formed around a particle or particulate matter. The layer or coating need not always be complete or uniform and need not necessarily lead to complete coverage of the particulate matter or particle surface. It is appreciated that upon repetition of the coating steps as the coating process proceeds a more uniform coating and more complete coverage of the particulate matter is obtained.

The term "dispersion," as used herein, in step (a) of the process refers to a solid dispersion of the particulate matter in the aqueous medium. Step (a) of the process can further comprise reducing the particle size of the particulate matter to the desired particle size, for example, by milling or homogenization.

The core (i.e., solid, BPO particulate matter) can be of any shape, for example, rod-like, plate-like, ellipsoidal, cubic, spherical shape, combinations thereof and the like.

Reference to the size of particles will be made through their $D_{90}$, which means that about 90% of the particles have the stated dimension or less (measured by volume). Thus, for example, for spherical particles stated to have a diameter of about 10 micrometer ("microns"), this means that the particles have a $D_{90}$ of about 10 microns. The $D_{90}$ can be measured by laser diffraction. For particles having a shape other than spheres, the $D_{90}$ refers to the mean average of the diameter of a plurality of particles.

In the case of cores having a spherical shape, the $D_{90}$ can be in the range of from about 0.3 to 90 microns, in some embodiments from about 0.3 to about 50 microns, in some other embodiments from about 1 to about 50 microns, in some further embodiments from about 5 to about 30 microns. As used herein, the phrase "$D_{90}$ can be in the range of from about 0.3 microns to about 90 microns" means about 90% by volume of the particles (in this case the particle's core) can be less than or equal to a value in the range of from about 0.3 microns to about 90 microns.

For generally cubic-shaped cores or cores having a shape resembling that of a cube, the mean size of a side can be in the range of from about 0.3 to about 80 microns, in some embodiments from about 0.3 to about 40 microns, in some further embodiments from about 0.8 to about 40 microns, in some further embodiments from about 4 to about 15 microns.

For rod-like shaped, ellipsoidal-shaped and plate-like shaped cores, the largest dimension (that of the longest axis) is typically in the range of from about 10 to about 100 microns, in some embodiments from about 15 to about 50 microns; and the smallest dimension is typically in the range of from about 0.5 to about 20 microns, in some further embodiments from about 2 to about 10 microns.

As used herein, unless otherwise indicated, the term "particle" refers to the metal oxide or semi-metal oxide coated particulate matter.

It is appreciated that some of the particles obtained by the process can at times be formed from two or more original particles of the solid BPO particulate and can accordingly include at times more than one core, such cores being separated from each other by a metal oxide region.

The weight of the solid BPO particulate (core material) based on the total weight of the particle can be in the range of from about 99% w/w to about 50% w/w, in some embodiments in the range of from about 97% w/w to about 50% w/w. The core material can be in a crystalline form, amorphous form, or combination thereof. The core material can be a cosmetic, pharmaceutical or an agrochemical active ingredient.

EXEMPLARY EMBODIMENTS

BPO-containing compositions were prepared following the various preparation methods described in U.S. Application Publication Nos. 2010/0016443, 2017/0281571 and 2018/0147165 and U.S. Pat. No. 9,687,465, the contents of which are incorporated herein, by reference, in their entirety.

Description:

A multi-center, open-label active- and vehicle-controlled study of encapsulated 5% benzoyl peroxide cream (E-BPO) and vehicle cream was performed to assess the long-term safety of E-BPO compared to vehicle. Study duration was up to 52 weeks (365 days), and the patients were at least 18 years of age.

Patients were admitted into the study after meeting all inclusion/exclusion criteria, including a clinical diagnosis of moderate to severe rosacea, and after obtaining written informed consent. Clinical and safety evaluations were performed at about baseline, about 2, about 4, about 8, about 12, about 16, about 20, about 24, about 28, about 32, about 36, about 40, about 44, about 48 and about 52 weeks. At each visit, a 5-point IGA scale of rosacea; rosacea erythema, and telangiectasia were performed and recorded. The study product was dispensed only to patients assessed as having "mild," "moderate" or "severe" (2, 3 or 4 on the IGA scale, respectively) at each measurement.

Dosing and Examination:

Encapsulated BPO cream (5%) was dispensed every 4 weeks. Patients applied the study product once daily, for up to 52 weeks, on the face in a thin layer to provide even distribution.

Safety was assessed at all visits, including: monitoring for any adverse effects (AE), including local and systemic AE; investigator Cutaneous Safety Assessment rating of dryness and scaling and Local Tolerability Assessments rating of itching and burning/stinging on a scale ranging from 0 (none) to 3 (severe).

Investigator Global Assessment (IGA):

Efficacy of 5% E-BPO in the treatment of moderate to severe rosacea was assessed using Investigator Global Assessment (IGA). The investigator performed the IGA Screening, Baseline, and Weeks 2, 4, 8, 12, 16, 20, 24, 28, 32, 36, 40, 44, 48 and 52 (end of study). The evaluator also assessed local application site irritation (dryness, scaling, itching and burning) at Baseline and Weeks 2, 4, 8, 12, 16, 20, 24, 28, 32, 36, 40, 44, 48 and 52 (end of study). Patients were eligible for IGA studies if they had facial rosacea with a global severity of a 3 (moderate) or a 4 (severe) on the IGA scale.

Safety Assessments:

Safety was evaluated by tabulations of adverse events (AEs), Cutaneous Safety Assessments for dryness and scaling, Local Tolerability Assessment for itching and burning.

Results:

The Baseline characteristics were similar among the treatment groups. Patients selected for the treatment groups of this study suffered from moderate and severe rosacea, and none of the patients presented as mild, clear or almost clear at the baseline visit.

Figure 1:
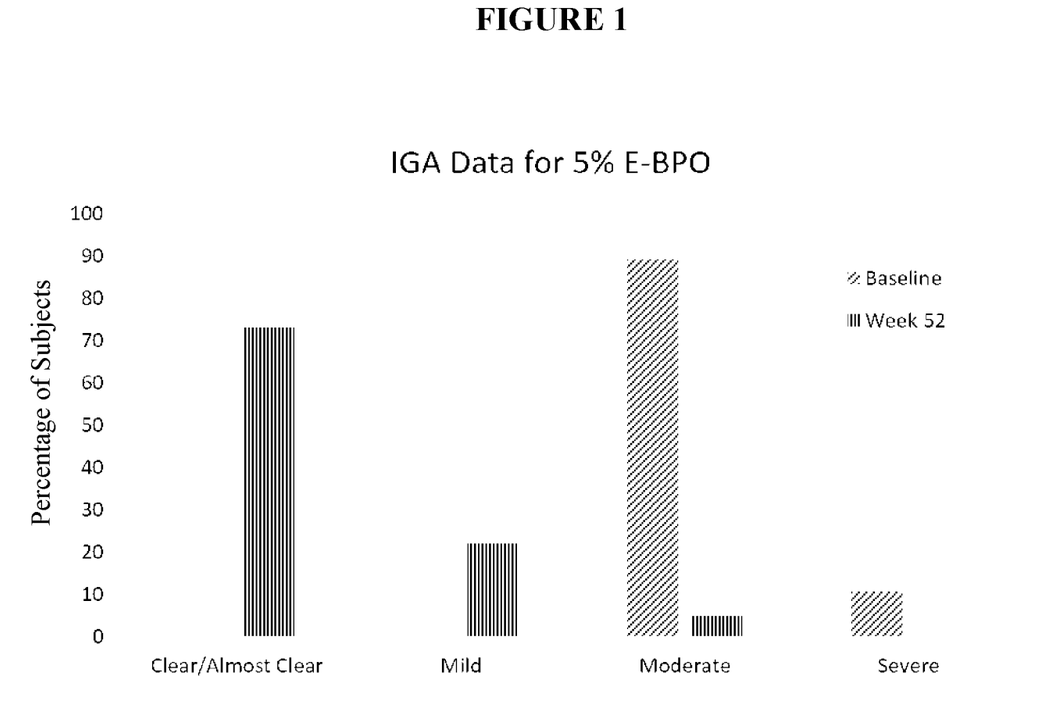
FIG. 1 is a graph presenting the Inventors Global Assessment (IGA) after treatment with a BPO composition for a period of 52 weeks compared with the baseline IGA values.

As used herein, the success rate in the treatment of severe rosacea is defined as a percentage increase in the number of subjects achieving clear or almost clear skin on the investor global assessment (IGA) scale after treatment with the pharmaceutical composition. While success is defined by the achievement of clear or almost clear skin, failure is defined as poste-treatment skin having mild, moderate and severe rosacea. The results are shown in Tables 1 and 2 below. The combined success and failure analysis is included in Table 3 below. A comparison of the percentage of patients with varying degrees of rosacea symptoms from clear/almost clear to severe at baseline and after 52 weeks of treatment with E-BPO is shown in FIG. 1. As the results demonstrate, long-term treatment with 5% E-BPO, even up to 52 weeks, has unexpectedly superior effects. For example, as many as about 75% of patients treated with 5% E-BPO show clear to almost clear symptoms. In comparison, the starting population of patients at baseline has a significantly higher percentage of patients, as many as 90% of study subjects, demonstrating moderate to severe rosacea symptoms.

TABLE 1

Investigator Global Assessment (Vehicle Cream)**

Percentage of patients in IGA category

|  | Clear | Almost clear | Mild | Moderate | Severe |
| --- | --- | --- | --- | --- | --- |
| Baseline* | 0.0 | 0.0 | 0.0 | 91.3 | 8.7 |
| Week 4 | 10.2 | 21.0 | 58.7 | 10.2 | 0.0 |
| Week 8 | 12.7 | 28.9 | 53.0 | 5.4 | 0.0 |
| Week 12 | 11.4 | 31.6 | 48.1 | 8.9 | 0.0 |
| Week 16 | 14.5 | 33.3 | 42.8 | 9.4 | 0.0 |

TABLE 1-continued

Investigator Global Assessment (Vehicle Cream)**

Percentage of patients in IGA category

|  | Clear | Almost clear | Mild | Moderate | Severe |
|---|---|---|---|---|---|
| Week 20 | 15.4 | 39.1 | 40.4 | 5.1 | 0.0 |
| Week 24 | 12.6 | 38.4 | 39.7 | 9.3 | 0.0 |
| Week 28 | 15.1 | 38.8 | 39.6 | 5.8 | 0.7 |
| Week 32 | 16.4 | 35.2 | 42.2 | 6.3 | 0.0 |
| Week 36 | 17.6 | 31.9 | 47.1 | 3.4 | 0.0 |
| Week 40 | 22.1 | 48.7 | 26.5 | 2.7 | 0.0 |

*The first 12 weeks of subjects who received the vehicle were not included in the long-term study analysis. Thus, Week 4 for these subjects corresponds to Week 16 after Baseline of the study, and Week 40 corresponds to Week 52 of the study. Common IGA was calculated for all patients that had a parallel treatment period (e.g. BL, week 4, week 8, week 12 . . . week 36 and week 40). For week 44, week 48 and week 52 only one group - patients that only received the study drug - was counted.
**Percentage for Weeks 4, 8, 12, 16, 20, 24, 28, 32, 36, 40, 44, 48 and 52 represent average values obtained from averaging the summary statistics generated from each imputed dataset. Multiple imputation (MCMC) used to impute missing values.

TABLE 2

Investigator Global Assessment (5% E-BPO + Vehicle Cream)**

Percentage of patients in IGA category

|  | Clear | Almost clear | Mild | Moderate | Severe |
|---|---|---|---|---|---|
| Baseline | 0.0 | 0.0 | 0.0 | 89.2 | 10.8 |
| Week 4 | 7.0 | 24.9 | 43.2 | 24.5 | 0.4 |
| Week 8 | 11.2 | 33.3 | 41.8 | 13.6 | 0.2 |
| Week 12 | 12.7 | 33.0 | 41.3 | 12.9 | 0.2 |
| Week 16 | 14.0 | 29.3 | 44.5 | 12.2 | 0.0 |
| Week 20 | 13.0 | 36.5 | 42.3 | 8.2 | 0.0 |
| Week 24 | 14.6 | 35.9 | 40.2 | 9.2 | 0.0 |
| Week 28 | 13.9 | 38.3 | 40.9 | 6.6 | 0.2 |
| Week 32 | 17.2 | 35.6 | 41.8 | 5.4 | 0.0 |
| Week 36 | 15.6 | 34.0 | 44.1 | 6.0 | 0.2 |
| Week 40 | 18.6 | 39.3 | 37.2 | 4.9 | 0.0 |
| Week 44 | 22.3 | 34.0 | 38.3 | 5.5 | 0.0 |
| Week 48 | 22.1 | 29.0 | 44.2 | 4.3 | 0.4 |
| Week 52 | 26.3 | 46.9 | 22.0 | 4.8 | 0.0 |

**Percentage for Weeks 2, 4, 8 and 12 represent average values obtained from averaging the summary statistics generated from each imputed dataset. Multiple imputation (MCMC) used to impute missing values.

TABLE 3

IGA Efficacy Analysis

|  |  | 5% E-BPO + Vehicle Cream | Vehicle Cream |
|---|---|---|---|
| Week 4 | Success | 31.9 | 31.1 |
|  | Failure | 68.1 | 68.9 |
| Week 8 | Success | 44.4 | 41.6 |
|  | Failure | 55.6 | 58.4 |
| Week 12 | Success | 45.7 | 43.0 |
|  | Failure | 54.3 | 57.0 |
| Week 16 | Success | 43.3 | 47.8 |
|  | Failure | 56.7 | 52.2 |
| Week 20 | Success | 49.5 | 54.5 |
|  | Failure | 50.5 | 45.5 |
| Week 24 | Success | 50.5 | 51.0 |
|  | Failure | 49.5 | 49.0 |
| Week 28 | Success | 52.2 | 54.0 |
|  | Failure | 47.8 | 46.0 |
| Week 32 | Success | 52.8 | 51.6 |
|  | Failure | 47.2 | 48.4 |
| Week 36 | Success | 49.7 | 49.6 |
|  | Failure | 50.3 | 50.4 |
| Week 40 | Success | 57.9 | 70.8 |
|  | Failure | 42.1 | 29.2 |
| Week 44 | Success | 56.3 | — |
|  | Failure | 43.8 | — |
| Week 48 | Success | 51.1 | — |
|  | Failure | 48.9 | — |
| Week 52 | Success | 73.2 | — |
|  | Failure | 26.8 | — |

Figure 2:
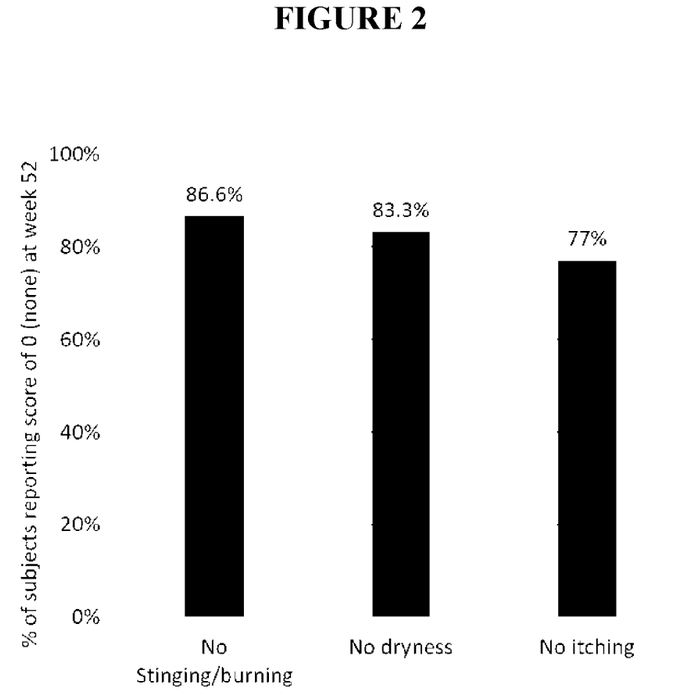
FIG. 2 is a graph presenting the local tolerability after treatment with a BPO composition for a period of 52 weeks.

Additionally, the study product, 5% E-BPO has excellent local tolerability, even after daily application for 52 weeks. A summary of cutaneous safety and tolerability evaluations of the study subjects is provided in Tables 4 and 5 below. The percentage of patients reporting no stinging/burning, dryness and itching (an IGA score of zero) after 52 weeks is at least about 75%, and preferably between about 75% to 85%, as shown in FIG. 2. Moreover, the tolerability of patients treated with 5% E-BPO is similar to patients treated with vehicle alone.

TABLE 4

Summary of Subcutaneous Safety and Tolerability Evaluations (Vehicle Cream)**

Percentage of patients in each category with no symptoms

|  | Dryness | Itching | Burning/Stinging |
|---|---|---|---|
| Baseline* | 46.5 | 44.2 | 57.0 |
| Week 4 | 59.3 | 71.3 | 80.2 |
| Week 8 | 66.3 | 76.5 | 85.5 |
| Week 12 | 67.7 | 75.3 | 79.1 |
| Week 16 | 68.6 | 78.6 | 90.6 |
| Week 20 | 71.8 | 74.4 | 88.5 |
| Week 24 | 72.8 | 71.5 | 84.1 |
| Week 28 | 69.8 | 79.9 | 87.8 |
| Week 32 | 71.1 | 69.5 | 82.0 |
| Week 36 | 68.9 | 73.1 | 84.0 |
| Week 40 | 67.3 | 69.9 | 86.7 |

*The first 12 weeks of subjects who received the vehicle were not included in the long-term study analysis. Thus, Week 4 for these subjects corresponds to Week 16 after Baseline of the study, and Week 40 corresponds to Week 52 of the study. Common IGA was calculated for all patients that had a parallel treatment period (e.g. BL, week 4, week 8, week 12 . . . week 36 and week 40). For week 44, week 48 and week 52 only one group - patients that only received the study drug - was counted.
**Percentage for Weeks 4, 8, 12, 16, 20, 24, 28, 32, 36, 40, 44, 48 and 52 represent average values obtained from averaging the summary statistics generated from each imputed dataset. Multiple imputation (MCMC) used to impute missing values.

TABLE 5

Summary of Subcutaneous Safety and Tolerability Evaluations (5% E-BPO + Vehicle Cream)**

Percentage of patients in each category with no symptoms

|  | Dryness | Itching | Burning/Stinging |
|---|---|---|---|
| Baseline | 46.4 | 42.1 | 58.7 |
| Week 4 | 60.8 | 66.2 | 74.3 |
| Week 8 | 66.5 | 72.2 | 80.3 |
| Week 12 | 67.8 | 70.6 | 77.0 |
| Week 16 | 64.4 | 76.0 | 86.0 |
| Week 20 | 68.5 | 75.0 | 89.2 |
| Week 24 | 69.6 | 73.1 | 84.2 |
| Week 28 | 72.2 | 79.9 | 89.1 |
| Week 32 | 69.6 | 78.3 | 90.6 |
| Week 36 | 70.6 | 78.2 | 86.2 |

TABLE 5-continued

Summary of Subcutaneous Safety and Tolerability
Evaluations (5% E-BPO + Vehicle Cream)**

| | Percentage of patients in each category with no symptoms | | |
|---|---|---|---|
| | Dryness | Itching | Burning/ Stinging |
| Week 40 | 70.8 | 76.0 | 89.1 |
| Week 44 | 73.4 | 75.8 | 89.1 |
| Week 48 | 69.7 | 73.2 | 88.7 |
| Week 52 | 70.8 | 77.0 | 86.6 |

**Percentage for Weeks 2, 4, 8 and 12 represent average values obtained from averaging the summary statistics generated from each imputed dataset. Multiple imputation (MCMC) used to impute missing values.

The above-discussed results demonstrate the unexpected superiority of the benzoyl peroxide composition described in this application in the long-term treatment of rosacea in patients in need of such treatment. These results also support the conclusion that, contrary to prevalent opinion, BPO is an excellent first line therapy for rosacea.

Although the exemplary embodiments of the present disclosure have been described in detail with reference to the accompanying examples and drawings, the present disclosure is not limited thereto and can be embodied in many different forms without departing from the technical concept of the present disclosure. Therefore, the exemplary embodiments of the present disclosure are provided for illustrative purposes only and are not intended to limit the technical concept of the present disclosure. The protective scope of the present disclosure should be construed based on any appended claims and combinations thereof, and all the technical concepts in the equivalent scope thereof should be construed as falling within the scope of the present disclosure. As various changes could be made in the above methods and compositions without departing from the scope of the invention, it is intended that all matter contained in the above description shall be interpreted as illustrative and not in a limiting sense. Other embodiments within the scope of the claims herein will be apparent to one skilled in the art from consideration of the specification or practice of the exemplary embodiments disclosed herein. It is intended that the specification be considered exemplary only, with the scope and spirit of the described subject matter being indicated by the claims.

What is claimed is:

1. A regimen for the long-term therapeutic treatment of rosacea, the regimen comprising topically applying to the skin of a subject in need of said treatment a pharmaceutical composition, the pharmaceutical composition comprising about 1% w/w to about 10% w/w benzoyl peroxide as an active ingredient, and a pharmaceutically acceptable carrier or excipient, wherein the benzoyl peroxide is the only active ingredient in said pharmaceutical composition, wherein said pharmaceutical composition is applied once daily for a period of about 52 weeks, to achieve, in a group of such subjects, a success rate of about 75%, wherein the success rate is defined as a percentage of the number of subjects achieving clear or almost clear skin on the investor global assessment (IGA) scale after treatment with the pharmaceutical composition.

2. The regimen of claim 1, wherein the benzoyl peroxide is the sole active ingredient administered to the subject during the duration of the regimen.

3. The regimen of claim 1, wherein the pharmaceutical composition comprises about 2.5% w/w to about 10% w/w of benzoyl peroxide.

4. The regimen of claim 3, wherein the pharmaceutical composition comprises about 5% w/w of benzoyl peroxide.

5. The regimen of claim 1, wherein the benzoyl peroxide is selected from a solid, solution or suspension form.

6. The regimen of claim 1, wherein the regimen is a first line therapy for the treatment of rosacea.

7. The regimen of claim 1, wherein the rosacea is any of erythematotelengietatic rosacea, papulopustular rosacea, phymatous rosacea or ocular rosacea.

8. The regimen of claim 1, wherein said pharmaceutical composition is a cream or an emulsion.

9. The regimen of claim 1, wherein said pharmaceutical composition is an extended release formulation.

10. The regimen of claim 9, wherein the extended-release effect is obtained by encapsulation, microencapsulation, microspheres or coating.

11. The regimen of claim 10, wherein the benzoyl peroxide is encapsulated or microencapsulated.

12. The regimen of claim 10, wherein the benzoyl peroxide is included in a microsphere or a coating.

13. The regimen of claim 1, wherein the rosacea is moderate to severe rosacea.

14. The regimen of claim 1, wherein a percentage of subjects having no adverse effects after treatment with the pharmaceutical composition after about 52 weeks is at least 75%.

15. The regimen of claim 14, where the percentage of subjects having no adverse effects after treatment with the pharmaceutical composition after about 52 weeks is from about 75% to about 85%.

16. The regimen of claim 1, wherein the adverse effect is selected from itching, burning, dryness, itching and a combination thereof.

* * * * *